(12) United States Patent
Tian et al.

(10) Patent No.: US 9,372,113 B2
(45) Date of Patent: Jun. 21, 2016

(54) REMOTE SENSING BASED ON OPTICAL FIBER DELIVERY AND COLLECTION

(71) Applicant: NEC Laboratories America, Inc., Princeton, NJ (US)

(72) Inventors: Yue Tian, Princeton, NJ (US); Ting Wang, West Windsor, NJ (US)

(73) Assignee: NEC Corporation (JP)

( * ) Notice: Subject to any disclaimer, the term of this patent is extended or adjusted under 35 U.S.C. 154(b) by 0 days.

(21) Appl. No.: 14/615,525

(22) Filed: Feb. 6, 2015

(65) Prior Publication Data

US 2015/0233761 A1  Aug. 20, 2015

Related U.S. Application Data

(60) Provisional application No. 61/940,958, filed on Feb. 18, 2014.

(51) Int. Cl.
| | |
|---|---|
| *G01J 3/00* | (2006.01) |
| *G01J 3/02* | (2006.01) |
| *G01N 21/25* | (2006.01) |
| *G01J 3/10* | (2006.01) |

(52) U.S. Cl.
CPC ............... *G01J 3/0218* (2013.01); *G01J 3/10* (2013.01); *G01N 21/255* (2013.01); *G01N 2201/062* (2013.01); *G01N 2201/06113* (2013.01); *G01N 2201/08* (2013.01)

(58) Field of Classification Search
CPC ................. G01J 3/02; G01J 3/28; G01J 3/42; G01N 21/31; G01N 21/552
USPC .................................................. 356/300–445
See application file for complete search history.

(56) References Cited

U.S. PATENT DOCUMENTS

| | | | |
|---|---|---|---|
| 7,800,755 B1* | 9/2010 | Poirier ...................... | G01J 4/04 356/367 |
| 2002/0075472 A1* | 6/2002 | Holton ................. | G01N 21/538 356/4.01 |
| 2014/0168631 A1* | 6/2014 | Haslim ................... | G01S 17/06 356/4.01 |

OTHER PUBLICATIONS

M. Nikodem et al., "Chirped Laser Dispersion Spectroscopy for Remote Open-Path Trace-Gas Sensing", Sensors 2012, 12, pp. 16466-16481, doi:10.3390/s121216466, www.mdpi.com/journal/sensors.

* cited by examiner

*Primary Examiner* — Abdullahi Nur
(74) *Attorney, Agent, or Firm* — Joseph Kolodka

(57) ABSTRACT

Active components in an optical spectroscopy based sensor are moved to a remote site and the light is guided between the remote site and the sensing site through optical fibers.

14 Claims, 3 Drawing Sheets

REMOTE SENSING BASED ON OPTICAL FIBER DELIVERY AND COLLECTION

RELATED APPLICATION INFORMATION

This application claims priority to provisional application Ser. No. 61/940,958 filed on Feb. 18, 2014, entitled "Remote sensing based on optical fiber delivery and collection", the contents thereof are incorporated herein by reference.

BACKGROUND

The present invention relates optical communications, and, more particularly, to remote sensing based on optical fiber delivery and collection.

In optical spectroscopy based sensing technologies, light sources, photodetectors and other active components, e.g. temperature controller, air pump, and ventilation, are usually included in the sensor heads on situ. If the sensors are required to operate in a severe environment, active components need additional environmental control facilities to maintain appropriate conditions, such as temperature, humidity, pressure etc. to guarantee proper operation of the sensors. And in some cases, it might be impossible or very hard to provide power supplies on site.

Complicated environmental control systems are equipped with or integrated in the sensors, which consumes more power and make the whole systems more bulky, hard to deploy in limited space and hard to maintain. Another solution is to launch the light beam into free space from a remote site, aim the light beam at the target. After interference with the target, the light beam is detected at another remote site or is reflected back by a mirror to the original remote site. In this case, the light path has to be straight and free of any obstacles, otherwise the light might be blocked, resulting in sensor failure. Therefore it has high requirement on sensor deployment.

Accordingly, there is a need for remote sensing based on optical fiber delivery and collection.

SUMMARY OF THE INVENTION

A method for optical spectroscopy based sensing of an object, including providing from a remote site a light source, the remote site being remote from a sensing site where an object to be subjected to optical based spectroscopy is located, feeding light from the light source over a feeding optical fiber to the remote site, coupling the light from the feeding fiber to free space where the light is scattered by the object for sensing, coupling the light that is scattered by the objet to be sensed into a collecting optical fiber, and guiding the light from the collecting fiber back to the remote site for detection and spectroscopic analysis, wherein with the above steps enable spectroscopic based sensing of a remotely located object to be performed with active optical components away from the remote site and at the sensing site for managing and maintaining the active components.

A system for optical spectroscopy based sensing of an object, including a light source for providing light from a remote site, the remote site being remote from a sensing site where an object to be subjected to optical based spectroscopy is located, a feeding optical fiber over which light from the light source is directed to the remote site, a collimator for coupling the light from the feeding fiber to free space where the light is scattered by the object for sensing; and another collimator for coupling the light that is scattered by the objet to be sensed into a collecting optical fiber for guiding the light from the collecting fiber back to the remote site for detection and spectroscopic analysis, wherein with the above steps enable spectroscopic based sensing of a remotely located object to be performed with active optical components away from the remote site and at the sensing site for managing and maintaining the active components.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present invention is directed to where at a remote site a light beam is launched into optical fiber, which guides the light to a target site for sensing. After passing through the target, the light beam is collected by optical fibers and guided back to the remote site for detection. The sensing heads at the target site are optical fibers for delivering and collecting the light and collimating lenses attached to the fiber facets to couple the light from fibers/free-space into free-space/fibers. Active components and power supplies can be moved to the remote site, where the environmental condition is less severe and the maintenance is easy to perform.

Figure 1:
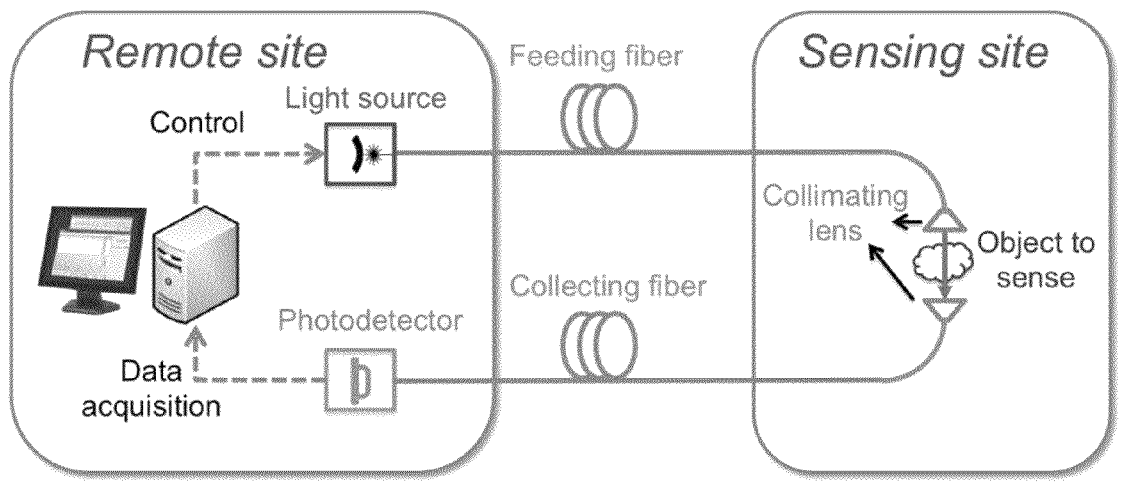
FIG. 1 depicts an optical configuration for remote sensing, in accordance with the invention.
Figure 2:
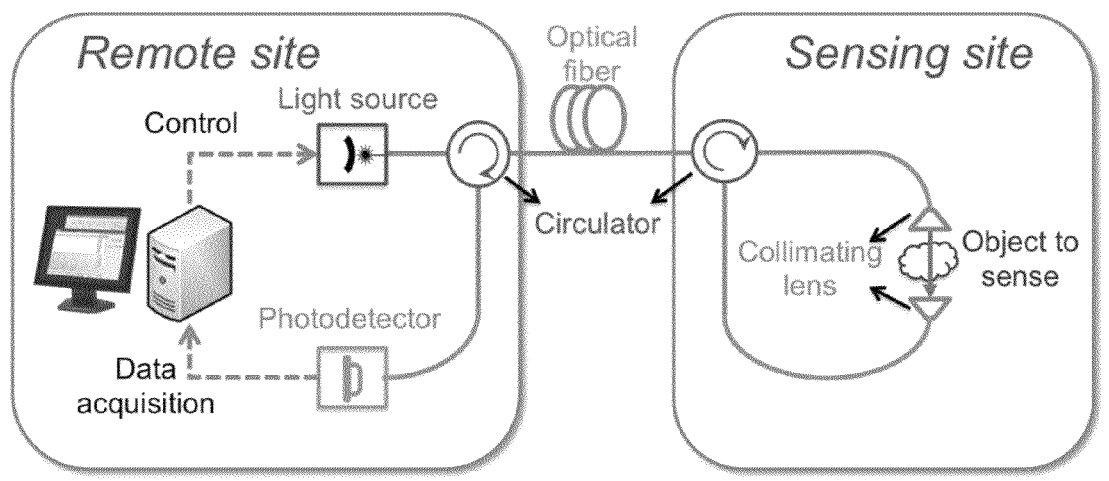
FIG. 2 is depicts an optical configuration for remote sensing in accordance with the invention.

Turning now to the optical configurations shown in FIGS. 1 and 2.

At a remote site, a light source, e.g. laser, LED, is controlled and emitted light is directed into an optical fiber (feeding fiber). The light for sensing is guided through the feeding fiber to a sensing site, where the light is coupled from the fiber to free space via a collimating lens. Then the light travels through or is scattered by an object that is being sensed, after which the light is coupled into another optical fiber (collecting fiber) via another collimating lens. The light is guided in the collecting fiber back to the remote site and detected by a photodetector.

The feeding fiber and collecting fiber can be replaced by one single fiber as well, as illustrated in FIG. 2. At the remote site, output light from the light source travels through an optical circulator and fed into the feeding/collecting fiber connecting remote site and sensing site. In the opposite direction, any light delivered by the feeding/collecting fiber back to remote site is routed by the circulator to the photodetector. Similarly at the sensing site, the light output from the feeding/collecting fiber is directed by the circulator to the collimating lens and the object, and then through the other collimating lens back to the circulator and coupled into the feeding/collecting fiber to the remote-site direction.

Figure 3:
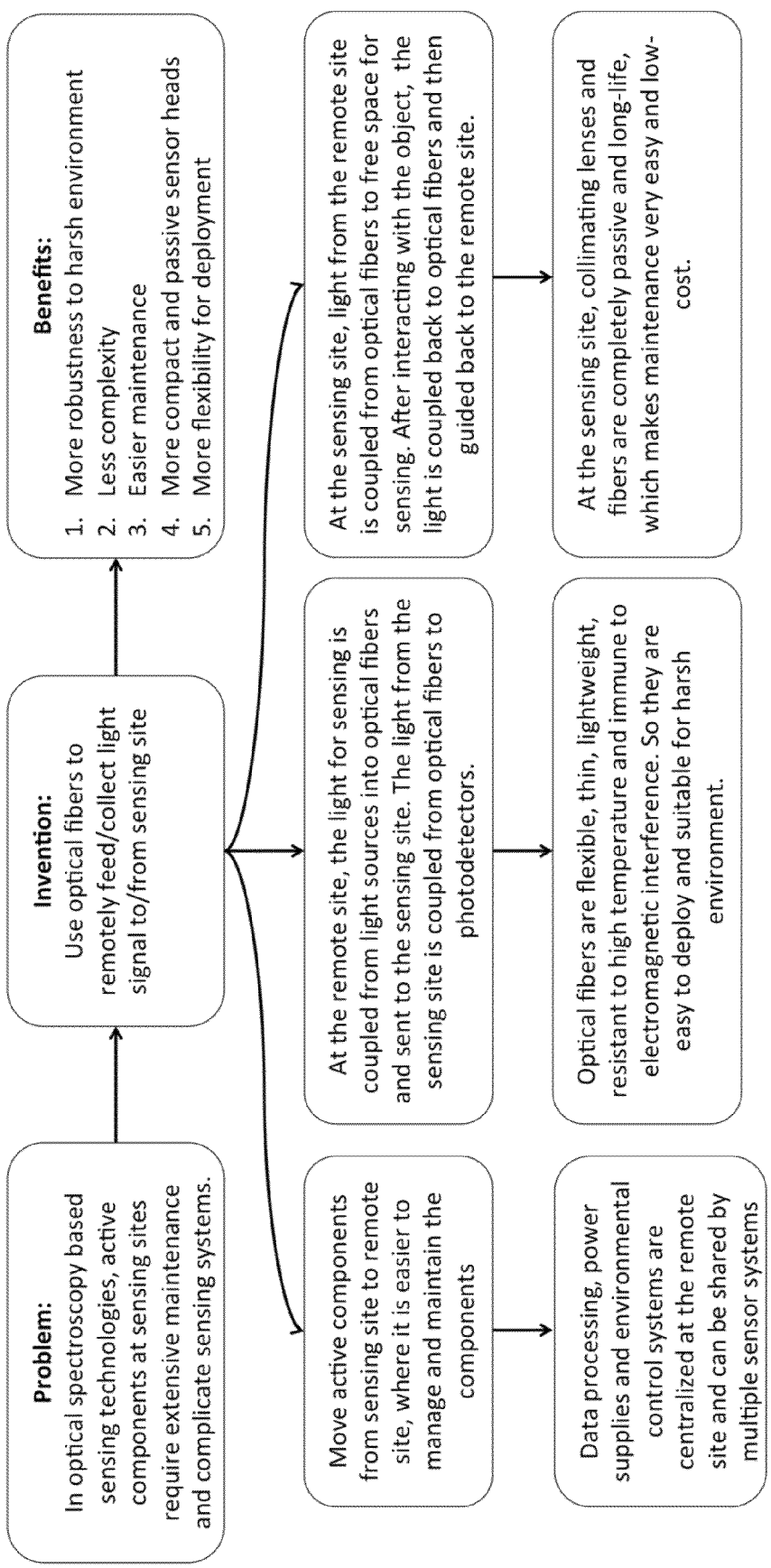
FIG. 3 is a diagram depicting key aspects of the invention.

FIG. 3 shows key aspects of the inventive remote sensing. In optical spectroscopy based sensing technologies, active components at sensing sites require extensive maintenance and complicated sensing systems. The invention uses optical fibers to remotely feed and collect the optical signal to and from a sensing site.

Active components are moved from the sensing site to the remote site where it is easier to manage and maintain the active components. Data processing, power supplies and environmental control systems are centralized at the remote site and can be shared by multiple sensor systems.

At the remote site, the light for sensing is coupled from optical fibers to free space for sensing. After interacting with the object to be sensed, the light is coupled back to optical fibers and then guided back to the remote site. Optical fibers are flexible, lightweight, thin, resistant to high temperatures and immune to electromagnetic interference. Thus they are easy to deploy and suitable for harsh environment.

At the sensing site, light from the remote site is coupled from optical fibers to free space for sensing. After interacting with the object, the light is coupled back to the optical fibers and then guided back to the remote site. At the sensing site, collimating lenses and fibers are completely passive and exhibit long life functionality, which makes maintenance very easy and low cost.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device. More details are discussed in U.S. Pat. No. 8,380,557, the content of which is incorporated by reference.

Figure 4:
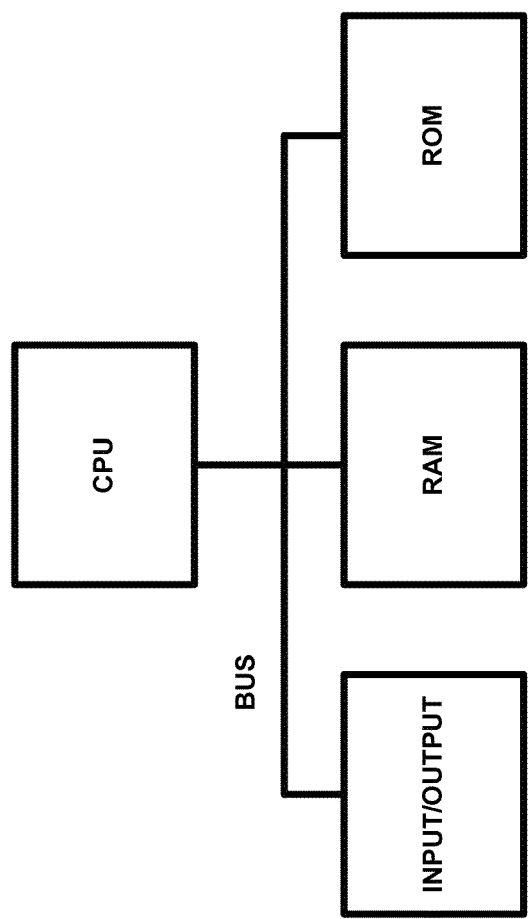
FIG. 4 shows an exemplary computer for carrying out the invention.

By way of example, a block diagram of a computer to support the invention is discussed next in FIG. 4. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

From the foregoing it can be appreciated from the present invention improves optical spectroscopy based sensing technologies with more robustness to severe environment situations, less complexity, easier maintenance, more compact and passive sensor heads, more flexibility for deployment.

Moving the active components to a remote site and using optical fibers to deliver/collect light signal between the remote site and sensing site are new. In most prior schemes, active components are mostly at the sensing site, close to the object. In some prior schemes, the active components are at a remote site, but the light signal is launched to the object in free space, in which case the light path has to be straight and there is a possibility that the light may be blocked by obstacles in the path.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for optical spectroscopy based sensing of an object, comprising the steps of:
   providing from a remote site a light source, the remote site being remote from a sensing site where an object to be subjected to optical based spectroscopy is located;
   feeding light from the light source over a feeding optical fiber to the sensing site;
   coupling the light from the feeding fiber to free space where the light is scattered by the object for sensing;
   coupling the light that is scattered by the object to be sensed into a collecting optical fiber; and
   guiding the light from the collecting fiber back to the remote site for detection and spectroscopic analysis;
   wherein light from the light source directed by the feeding optical fiber is further directed by a circulator to a collimating lens and the object, and then through another collimating lens back to the circulator and coupled into the feeding optical fiber to a remote-site direction, and
   such that spectroscopic based sensing of a remotely located object is performed wherein all active optical components are located at the remote site and the object undergoing optical spectroscopic analysis is located at the sensing site; and
   wherein the feeding fiber and the collecting fiber are the same one single fiber that optically connects the remote site including the light source and any detectors to the sensing site including the object to be spectroscopically analyzed.

2. The method of claim 1, wherein the feeding and collecting fiber are coupled to respective optical circulators.

3. The method of claim 1, wherein at the remote site, light from the light source travels through an optical circulator and fed into the feeding or collecting fiber connecting the remote site and sensing site, and in the opposite direction, any light delivered by the feeding or collecting fiber back to the remote site is routed by the circulator to a photodetector.

4. The method of claim 2, wherein at the sensing site, the light from the feeding or collecting fiber is directed by the circulator to a collimating lens and the object, and then through another collimating lens back to the circulator and coupled into the feeding or collecting fiber to the remote-site direction.

5. The method of claim 1, wherein with the inventive steps enable data processing, power supplies and environmental control systems to be centralized at the remote site and available for sharing by multiple sensor systems.

6. The method of claim 1, wherein the inventive steps enable use of optical fibers that are flexible, thin, lightweight and immune to electromagnetic interference that are easy to deploy, suitable for harsh sensing environments and improve spectroscopic sensing of an object.

7. The method of claim 1, wherein at the sensing site, collimating lenses for the coupling steps and fibers are completely passive and have long life functionality enabling easy maintenance and low cost for spectroscopic based sensing of an object remotely located.

8. A system for optical spectroscopy based sensing of an object, comprising:
- a lightsource for providing light from a remote site, the remote site being remote from a sensing site where an object to be subjected to optical based spectroscopy is located;
- a feeding optical fiber over which light from the light source is directed to the sensing site;
- a collimator for coupling the light from the feeding fiber to free space where the light is scattered by the object for sensing; and
- another collimator for coupling the light that is scattered by the object to be sensed into a collecting optical fiber for guiding the light from the collecting fiber back to the remote site for detection and spectroscopic analysis;
- wherein the light from the light source directed by the feeding optical fiber is further directed by a circulator to a collimating lens and the object, and then through another collimating lens back to the circulator and coupled into the feeding optical fiber to a remote-site direction;
- such that spectroscopic based sensing of a remotely located object is performed wherein all active optical components are located at the remote site and the object undergoing optical spectroscopic analysis is located at the sensing site;
- wherein the feeding fiber and the collecting fiber are the same one single fiber that optically connects the remote site including the light source and any detectors to the sensing site including the object to be spectroscopically analyzed.

9. The system of claim 8, wherein the feeding and collecting fibers are coupled to respective optical circulators.

10. The system of claim 8, wherein at the remote site, light from the light source travels through an optical circulator and fed into the feeding or collecting fiber connecting the remote site and sensing site, and in the opposite direction, any light delivered by the feeding or collecting fiber back to the remote site is routed by the circulator to the photodetector.

11. The system of claim 8, wherein at the sensing site, the light from the feeding or collecting fiber is directed by the circulator to a collimating lens and the object, and then through another collimating lens back to the circulator and coupled into the feeding or collecting fiber to the remote-site direction.

12. The system of claim 8, wherein the system enables data processing, power supplies and environmental control systems to be centralized at the remote site and available for sharing by multiple sensor systems.

13. The system of claim 8, wherein the system enables use of optical fibers that are flexible, thin, lightweight and immune to electromagnetic interference that are easy to deploy, suitable for harsh sensing environments and improve spectroscopic sensing of an object.

14. The system of claim 8, wherein at the sensing site, collimating lenses for the coupling steps and fibers are completely passive and have long life functionality enabling easy maintenance and low cost for spectroscopic based sensing of an object remotely located.

* * * * *